March 5, 1974 W. A. WARRINER Plant Pat. 3,508
ROSE PLANT
Filed Aug. 11, 1972
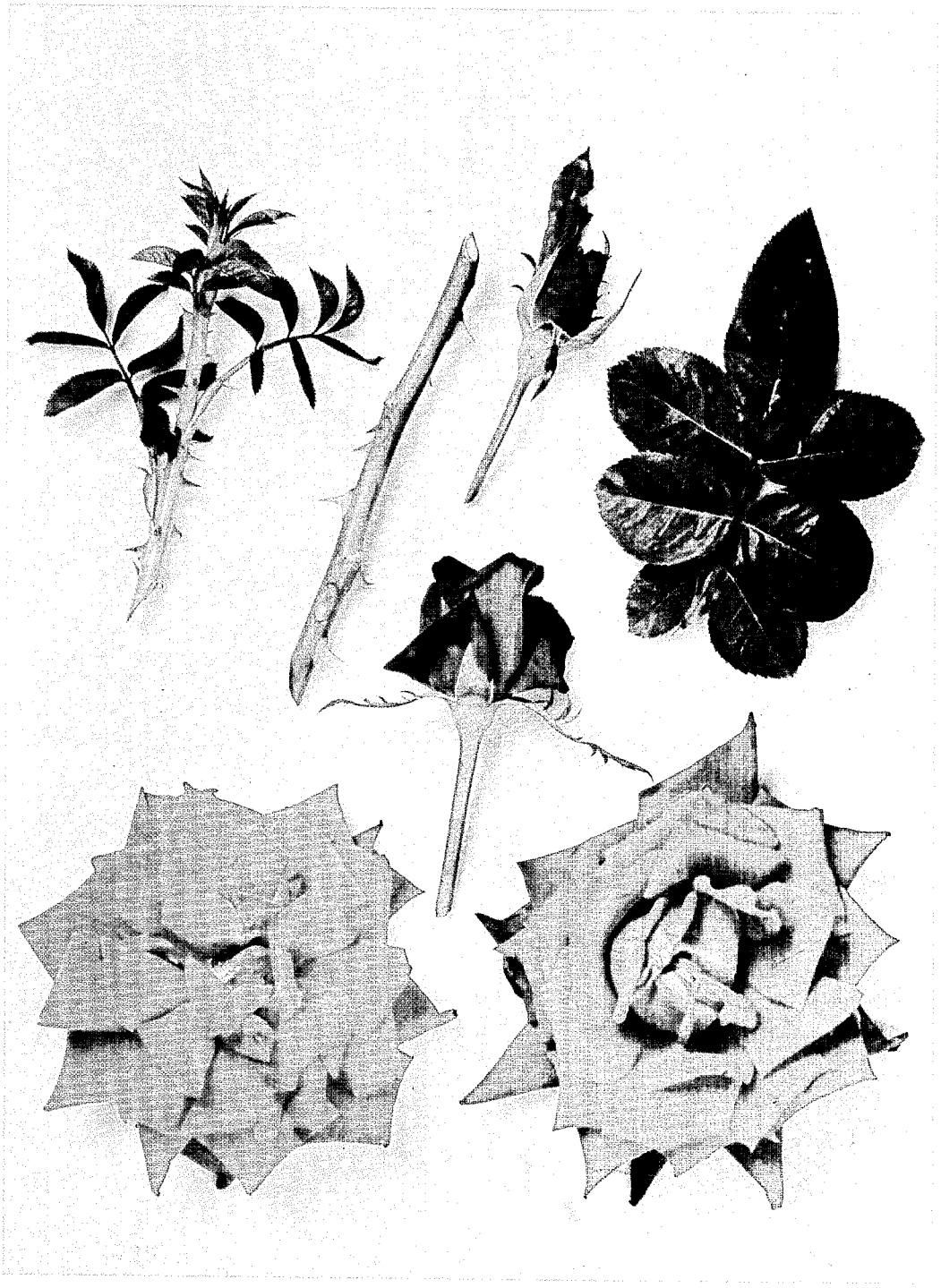

United States Patent Office

Plant Pat. 3,508
Patented Mar. 5, 1974

3,508
ROSE PLANT

William A. Warriner, Tustin, Calif., assignor to Jackson & Perkins Company, Medford, Oreg.

Filed Aug. 11, 1972, Ser. No. 279,815
Int. Cl. A01h *5/00*
U.S. Cl. Plt.—21 1 Claim

The present invention relates to a new and distinct variety of rose plant of the hybrid tea class which was originated by me by crossing a seedling (Siren × Chrysler Imperial) by a seedling (Carrousel × Chrysler Imperial).

The primary objective of this breeding was to produce a new rose variety of robust growth and large intensely red blooms.

This objective was substantially achieved as evidenced by the following unique combination of characteristics which are outstanding in this new variety and which distinguish it from its parents as well as from all other varieties of which I am aware:

(1) A vigorous, upright, well branched habit of growth.
(2) Excellent suitability as a garden variety because of its abundance of blooms borne on long upright stems.
(3) Uniform intense color of blooms, closely resembling Cardinal Red (822), with darker petal edges.
(4) A strong, sweet fragrance.

Asexual reproduction of this new variety by budding, as performed at Wasco, California, proves that the foregoing characteristics and distinctions reproduce true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling
*Seed parent.*—Siren × Chrysler Imperial.
*Pollen parent.*—Carrousel × Chrysler Imperial.
Classification:
*Botanic.*—*Rosa hybrid.*
*Commercial.*—Hybrid tea.

FLOWER

Observations were made at Irvine, Calif. in mid-April, 1972, in the afternoon.
Blooming habit: Recurrent—continuous.
Bud:
*Size.*—1½ inches when petals start to unfurl.
*Form.*—Ovoid to globular.
*Color.*—When sepals first divide near Cardinal Red (822) with occasional darker areas near petal tips. When half blown; inside of petals near Currant Red (821), darker shading near base of petal with small (⅛"), sharply defined area at point of attachment colored Canary Yellow (2/1); reverse of petals near, slightly lighter than Cardinal Red (822/3).
*Sepals.*—Color: Outer surface—Scheeles Green (860/1). Inner surface—Scheeles Green (860/1) with much white tomentum. Three appendaged sepals lightly appendaged. Two unappendaged sepals smooth edged.
*Receptacle.*—Color: Scheeles Green (860/1). Shape: Funnel. Size: Large, broad. Surface: Smooth.

*Peduncle.*—Length: Short. Surface: Smooth. Color: Scheeles Green (860/1) Strength: Stiff, erect.
*Opening.*—Petals slightly curled, opens slowly.
Bloom:
*Size.*—Large. Average size when fully expanded, 4½–5 inches.
*Borne.*—Singly.
*Stems.*—Long, strong.
*Form.*—When first open, high centered. Permanence—outer petal edges slightly curled.
*Petalage.*—Number of petals under normal conditions 45–50.
*Color.*—Center of flower: Upper side of petals Cardinal Red (822). Reverse of petals slightly lighter than Cardinal Red (822/3). Outer petals: Upper side of petals same. Base of petals: Very small Canary Yellow (2/1) area at point of attachment. General tonality from a distance, Cardinal Red (822). No variegations.
*Discoloration.*—No discoloration at end of first day. By third day petals darken slightly on tips.
*Fragrance.*—Strong.
Petals:
*Texture.*—Thin.
*Surface.*—Inside—satiny. Reverse—satiny.
*Shape.*—Round.
*Form.*—Edges slightly quilled.
*Arrangement.*—Informal.
*Petaloids in center.*—Few.
*Persistence.*—Drop off cleanly.
*Lastingness.*—On the plant—long. As cut flower—long.
Reproductive parts:
*Stamens, anthers.*—Large. Color—Eyythrite Red (0027/2) in center, edges Chinese Yellow (606/1). Arrangement—regular around styles.
*Stamens, filaments (threads).*—Long. Color—mostly Signal Red (719/3). Basal and Lemon Yellow (4/2).
*Pollen.*—Gold yellow.
*Styles.*—Loosely separated, of uneven lengths.
*Stigmas.*—Color—Amber Yellow (505/2).
*Ovaries.*—All enclosed in calyx.
Fruit: (Not observed.)

PLANT

Form: Bush.
Growth: Very vigorous, upright, branching.
Foliage: Number of leaflets on normal mid-stem leaves, 5 or 7.
*Size.*—Very large.
*Quantity.*—Abundant.
*Color.*—New foliage: Near but lighter than Garnet Brown (00918/3). Old foliage: Near Parsley Green (00962/1).
Leaflets:
*Shape.*—Oval.
*Texture.*—Leathery. Ribs and veins—prominent.
*Edge.*—Serrated.
*Serration.*—Single, small.
*Petiole—(rachis).*—Color — reddish. Underside—prickles.
*Stipules.*—Medium, smooth.
*Disease resistance.*—Susceptible to mildew under normal growing conditions at Irvine, Calif.
Wood:
*New wood.*—Color—light green at very end, changing to Garnet Brown (00918/3) 4–5 inches from tip, remains Garnet Brown until leaves mature and wood hardens. Bark—smooth.
*Old wood.*—Color—green. Bark—smooth.

Prickles:

*Quantity.*—On main stalks—ordinary. On laterals—ordinary.

*Form.*—Broad based, long, hooked downward.

*Color when young.*—Lighter than new foliage.

*Position.*—Irregular.

Small prickles:

*Quantity.*—On main stalks—none. On laterals—none.

I claim:

1. A new and distinct variety of rose plant of the hybrid tea class, substantially as herein shown and described, characterized particularly as to novelty by the unique combination of its vigorous, upright and branched plant, abundantly bearing fragrant blooms of Cardinal Red whose petal edges often are darker.

No references cited.

ROBERT E. BAGWILL, Primary Examiner